United States Patent [19]
Leverett et al.

[11] Patent Number: 5,980,904
[45] Date of Patent: Nov. 9, 1999

[54] SKIN WHITENING COMPOSITION CONTAINING BEARBERRY EXTRACT AND A REDUCING AGENT

[75] Inventors: Jesse C. Leverett, Rockford; Jeffrey M. Dornoff, Grand Rapids, both of Mich., .

[73] Assignee: Amway Corporation, Mich.

[21] Appl. No.: 09/195,577

[22] Filed: Nov. 18, 1998

[51] Int. Cl.$^6$ .................................................. A01N 65/00
[52] U.S. Cl. .......................................................... 424/195.1
[58] Field of Search ........................................... 424/195.1

[56] References Cited

U.S. PATENT DOCUMENTS

| | | |
|---|---|---|
| 4,500,510 | 2/1985 | Goldstein . |
| 4,814,351 | 3/1989 | Mathews et al. . |
| 4,826,691 | 5/1989 | Prochnow . |
| 4,883,654 | 11/1989 | Young . |
| 4,994,265 | 2/1991 | White . |
| 5,062,894 | 11/1991 | Schwartz et al. . |
| 5,320,834 | 6/1994 | Ounanian et al. . |
| 5,425,954 | 6/1995 | Thompson et al. . |
| 5,506,290 | 4/1996 | Shapero . |
| 5,595,731 | 1/1997 | Vallieres . |

FOREIGN PATENT DOCUMENTS

| | | |
|---|---|---|
| 1184756 | 4/1985 | Canada . |
| 1192108 | 8/1985 | Canada . |
| 1303512 | 6/1992 | Canada . |
| 2123039 | 11/1994 | Canada . |
| 2178171 | 10/1997 | Canada . |
| 1100904 | 4/1995 | China . |
| 244180 | 11/1987 | European Pat. Off. . |
| 317281 | 5/1989 | European Pat. Off. . |
| 342924 | 11/1989 | European Pat. Off. . |
| 379805 | 8/1990 | European Pat. Off. . |
| 385374 | 9/1990 | European Pat. Off. . |
| 518772 | 12/1992 | European Pat. Off. . |
| 547790 | 6/1993 | European Pat. Off. . |
| 572764 | 12/1993 | European Pat. Off. . |
| 628422 | 12/1994 | European Pat. Off. . |
| 741172 | 11/1996 | European Pat. Off. . |
| 755670 | 1/1997 | European Pat. Off. . |
| 763538 | 3/1997 | European Pat. Off. . |
| 767187 | 4/1997 | European Pat. Off. . |
| 816440 | 1/1998 | European Pat. Off. . |
| 2676645 | 11/1992 | France . |
| 2735688 | 12/1996 | France . |
| 2753374 | 3/1998 | France . |
| 2757058 | 6/1998 | France . |
| 4227806 | 2/1993 | Germany . |
| 196 50 620 | 1/1998 | Germany . |
| 50288 | 7/1981 | Hungary . |
| 56-092298 | 7/1981 | Japan . |
| 62-148426 | 7/1987 | Japan . |
| 2062833 | 3/1990 | Japan . |
| 2169501 | 6/1990 | Japan . |
| 4059711 | 2/1992 | Japan . |
| 7126146 | 5/1995 | Japan . |
| 2000807 | 10/1993 | Russian Federation . |
| 2001624 | 10/1993 | Russian Federation . |
| 2020950 | 10/1994 | Russian Federation . |
| 2021342 | 10/1994 | Russian Federation . |
| 2027751 | 1/1995 | Russian Federation . |
| 2040271 | 7/1995 | Russian Federation . |
| 2053265 | 1/1996 | Russian Federation . |
| 2064301 | 7/1996 | Russian Federation . |
| 2066195 | 9/1996 | Russian Federation . |
| 2097044 | 11/1997 | Russian Federation . |
| 2098118 | 12/1997 | Russian Federation . |
| 660451 | 4/1987 | Switzerland . |
| 660452 | 4/1987 | Switzerland . |
| 660453 | 4/1987 | Switzerland . |
| 660454 | 4/1987 | Switzerland . |
| 863633 | 9/1981 | U.S.S.R. . |
| 976934 | 11/1982 | U.S.S.R. . |
| 1165403 | 7/1985 | U.S.S.R. . |
| 1790939 | 1/1993 | U.S.S.R. . |
| 1790945 | 1/1993 | U.S.S.R. . |
| 2110084 | 6/1983 | United Kingdom . |
| 2236760 | 4/1991 | United Kingdom . |
| 2283914 | 5/1995 | United Kingdom . |
| WO 91/17436 | 11/1991 | WIPO . |
| WO 92/01115 | 1/1992 | WIPO . |
| WO 92/19951 | 11/1992 | WIPO . |
| WO 94/07532 | 4/1994 | WIPO . |
| WO 94/09757 | 5/1994 | WIPO . |
| WO 94/09796 | 5/1994 | WIPO . |
| WO 94/15580 | 7/1994 | WIPO . |
| WO 94/25001 | 11/1994 | WIPO . |
| WO 96/06613 | 3/1996 | WIPO . |
| WO 96/14743 | 5/1996 | WIPO . |
| WO 96/25916 | 8/1996 | WIPO . |
| WO 96/28138 | 9/1996 | WIPO . |
| WO 97/02807 | 1/1997 | WIPO . |
| WO 97/06777 | 2/1997 | WIPO . |
| WO 97/16381 | 5/1997 | WIPO . |
| WO 97/24031 | 7/1997 | WIPO . |
| WO 97/27941 | 8/1997 | WIPO . |
| WO 97/28237 | 8/1997 | WIPO . |
| WO 98/02740 | 1/1998 | WIPO . |

*Primary Examiner*—Herbert J. Lilling
*Attorney, Agent, or Firm*—Brinks Hofer Gilson & Lione; G. Peter Nichols

[57] ABSTRACT

A skin-whitening composition that includes bearberry extract and a reducing agent. The composition can be topically applied to the human skin and can include one or more whitening agents in combination with bearberry extract and the reducing agent to achieve an enhanced whitening effect. A method of whitening human skin includes topically applying to the skin a composition containing bearberry extract and a reducing agent in an amount and for a period of time sufficient to visibly whiten the skin. The method includes incorporating bearberry extract and the reducing agent with known whitening agents and applying to the skin in an amount and for a period of time sufficient to visibly whiten the skin.

19 Claims, No Drawings

SKIN WHITENING COMPOSITION CONTAINING BEARBERRY EXTRACT AND A REDUCING AGENT

BACKGROUND OF THE INVENTION

The present invention relates to a skin-whitening composition for external use containing bearberry extract and a reducing agent and to a method of whitening skin by topically applying a composition containing an effective amount of bearberry extract and a reducing agent.

Skin color is primarily determined by the amount of melanin present in the skin. Thus, in recent years, cosmetic compositions have been developed to reduce the amount of melanin in the skin and therefore, whiten the skin. These development efforts have focused on whitening agents that inhibit the function and activity of tyrosinase, which plays an important role in the biosynthesis of melanin. For example, it has been proposed to incorporate into cosmetic compositions tyrosinase activity inhibitors such as hydroquinone, vitamin C and its derivatives, kojic acid, arbutin, glutathione, cysteine, and mulberry extract, among others.

Despite the efficacy of the above compounds in producing whiter skin, alternatives that are more effective are continually being sought. It has now found that skin-whitening compositions that contain bearberry can be improved by adding a reducing agent such as a formaldehyde-donating compound to the composition. It is believed that the reducing agent reduces the tyrosinase, which surprisingly results in a dramatically increased efficacy in the whitening effect of the composition.

In addition, it is believed that the reducing agent may be able to alter the chemical composition of certain amino acids, of which several are key to the process of melanin production. As a result, increased skin whitening efficacy is obtained.

SUMMARY OF THE INVENTION

It is an object of the present invention to provide compositions that include bearberry extract and a reducing agent, are suitable for external application, and prevent or inhibit the formation of melanin in the skin and thus whiten the skin. Another object is to enhance and accelerate the development of the whitening and beautifying effect exhibited by bearberry extract by adding a reducing agent such as diazolidinyl urea.

The present invention also includes a method of whitening the skin that comprises topically applying to the skin a composition containing bearberry extract and an effective amount of a reducing agent for a period of time sufficient to visibly whiten the skin. In a preferred embodiment, the reducing agent is a formaldehyde-donating compound. The term formaldehyde-donating compound refers to those compounds that can contribute a formaldehyde moiety when put into a cosmetic carrier. For example, the formaldehyde contributing compound may be selected from the group consisting of formaldehyde, 2-bromo-2-nitopropane-1,3-diol, glutaraldehyde, quaternium-15, polymethoxybicylic oxazolidine, DM hydantoin, MDM hydantoin, DMDM hydantoin, and allantoin-formaldehyde condensation products, including diazolidinyl urea and imidazolidinyl urea, and mixtures thereof. In a more preferred embodiment, the reducing agent is diazolidinyl urea, imidazolidinyl urea, or a mixture thereof.

The bearberry extract combined with the reducing agent acts as a whitening agent. Other whitening agents can be included in the skin-whitening composition. Examples of such agents include tyrosinase inhibitors, free radical scavengers, and mixtures thereof. Some tyrosinase inhibitors include, but are not limited to, arbutin, lemon extract, cucumber extract, mercaptosuccinic acid, mercaptodextran, kojic acid, derivatives of kojic acid, vitamin C, derivatives of vitamin C, hydroquinone, glutathione, cysteine, mulberry extract and its derivatives, licorice extract and its derivatives, and mixtures thereof.

In the whitening composition according to the present invention, the amount of bearberry extract and its reducing agent cannot be absolutely specified because it varies according to the form of preparation. However, bearberry is generally used in an amount from about 0.001% to about 99%, preferably from about 0.01% to about 50%, desirably from about 0.1% to about 25%, more preferably from about 0.2% to about 10%, most preferably from about 1% to about 5%. The reducing agent is generally used in an amount from about 0.001% to about 99%, preferably from about 0.01% to about 50%, desirably from about 0.1% to about 25%, more preferably from about 0.01% to about 1.00%, and most preferably from about 0.10% to about 0.50%.

It is noted that, unless otherwise stated, all percentages given in this specification and the appended claims refer to percentages by weight.

DETAILED DESCRIPTION OF THE PREFERRED EMBODIMENTS

In accordance with the present invention, a skin-whitening composition is provided that comprises bearberry extract and a reducing agent as active ingredients.

Bearberry extract is an extract from *Arctostaphylos uva-ursi*. Preferably, the bearberry extract is obtained from Pentapharm. It is a glycolic extract standardized to >50 tyrosinase inhibition units per milliliter (TyIU/ml).

The reducing agent is a formaldehyde-donating compound. The formaldehyde donating compounds function well as reducing agents to reduce sulf-hydro and amine functional groups. In addition, the reducing agents act to competitively interfere with the oxidation reactions leading to the formation of melanin from tyrosine. The formaldehyde donating compounds are selected from the group consisting of formaldehyde, 2-bromo-2-nitopropane-1,3-diol, glutaraldehyde, quaternium-15, polymethoxybicylic oxazolidine, DM hydantoin, MDM hydantoin, DMDM hydantoin, and allantoin-formaldehyde condensation products, including diazolidinyl urea and imidazolidinyl urea, and mixtures thereof. In a more preferred embodiment, the formaldehyde-donating compound is selected from the group consisting of diazolidinyl urea, imidazolidinyl urea, or a mixture thereof.

It is believed that a skin-whitening composition containing bearberry extract can achieve a higher efficacy of whitening skin if complemented by a reducing agent according to the present invention. As a result, a higher degree of skin-whitening activity can be achieved with a lower level of the bearberry extract.

It is further believed that a composition containing bearberry extract and a reducing agent according to the present invention may exhibit synergism by enhancing the skin whitening effect of the known skin whiteners. This effect may be further augmented by the addition of one or more substances having a known whitening effect.

For this reason, the composition of the present invention that includes bearberry extract and a reducing agent is preferably augmented with other whitening agents. The whitening agents useful in the present invention are believed to include all the known whitening agents and those that may be developed in the future. Although it may not be possible to identify and list all known whitening agents, the following whitening agents are mentioned and for purposes of the present invention are preferred: tyrosinase inhibitors, free radical scavengers, chelating agents, and mixtures thereof.

Some tyrosinase inhibitors include, but are not limited to, arbutin, orange extract, lemon extract, cucumber extract, mercaptosuccinic acid, mercaptodextran, kojic acid, derivatives of kojic acid, vitamin C, derivatives of vitamin C, hydroquinone and derivatives of hydroquinone, glutathione, cysteine and its derivatives such as N-acetyl-L-cysteine and those described in U.S. Pat. No. 5,296,500 the relevant portions of which are incorporated herein by reference, mulberry extract and its derivatives, licorice extract and its derivatives, rosemary extract and its derivatives, and mixtures thereof.

The kojic acid or its esters may be represented by the formula:

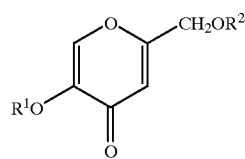

wherein $R^1$ and $R^2$ are the same or different, and each is hydrogen atom or an acyl group of 3 to 20 carbon atoms.

Non-exclusive examples of the esters are, for instance, kojic acid monoesters such as kojic acid monobutyrate, kojic acid monocaprate, kojic acid monopalmitate, kojic acid monostearate, kojic acid monocinnamoate and kojic acid monobenzoate; kojic acid diesters such as kojic acid dibutyrate, kojic acid dipalmitate, kojic acid distearate and kojic acid dioleate. A preferred monoester is an ester in which an OH group at 5-position of kojic acid is esterified. Esterification can improve stabilities against pH or sun light, while maintaining a melanin synthesis-inhibiting activity equal to that of kojic acid.

The free radical scavengers may include, but are not limited to ascorbic acid (vitamin C) and its derivatives, vitamin E, superoxide dismutase, acerola cherry extracts, acerola cherry fermentates.

The vitamin C and its derivatives may be present in any isomeric form. For example, they can all be in cis configurations, they can all be in trans configurations, or they can be in a mixture of cis and trans configurations.

Non-exclusive examples of the vitamin C derivatives are, for instance, the alkyl esters of L-ascorbic acid where the alkyl portion has from 8 to 20 carbon atoms. For example, such esters include, but are not limited to L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate, tetrahexyl decyl ascorbate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; their salts with alkaline earth metals such as calcium and magnesium. They can be used alone or in a mixture of two or more.

Other whitening agents may include gingko extract, carob extract, rose fruit extract, geranium herb extract, Perilla extract, cinnamon extract, sweet marjoram extract, Arnica extract, Concha Blanca extract, cola ed Caballo, Piri-Piri, Pinon Negro, Pinon Blanco, extracts of clove, alfalfa, Baliospermum montanum, Melia azadirachta, convolvulus arvensis, Gaiyo, Sansonin, Syuroyo, Seimkko, Soukyo, Taiso, Hakusempi, Woodfordia fructosa, Lagerstroemia speciosa, passiflorine, tepezcohite, amoule, Hobiyu, Baffalo Uri, Achote, Guayule, Adhatoda, Cymbopogon nardus, Desmodium gangeticum, Murraya koenigii, Smilax zeylanica, Gastrodia elata, Karukeija, Biota orientalis, Kichiascoporia, Arecatachu, Phyllostachys Nigra leaves, Atractylodes japonica, Koidzumi, Tila, Camotede Azafran, Jamaica, Poleo verde, Navo negro, Cyperus, Kanzo, Broussonetia, Karojitsu, Trichosanthis Radix, Dioscorea Phizoma, and Aquilliaria.

Other whiteners may include teprenone, dihydroxyisoquinoline, indomethacin, 3-hydroxymanule, vitamin K (such as vitamin K1–K7, its homologues, salts, and derivatives), thiazolidinone derivatives, and kynurenine and its derivatives and salts.

Another substance that may be useful in the present invention is mercaptodextran. Mercaptodextran is a polythiol that can be synthesized by thiolating a dextran compound using for example N-acetylhomocysteine thiolactone. The dextrans may have any suitable molecular weight from about 500 to 500,000. The mercaptodextrans useful in the present invention can be prepared according to the method set forth in Eldjarn, L. & E. Jellum: Organomercurialpolysaccharide, a chromatographic material for the separation and isolation of SH-proteins; *Acta Chem. Scand.*, 17:2610–21 (1963), and/or Jellum, E., J. Aaseth & L. Eldjarn: Mercaptodextran, a metal chelating and disulphide-reducing polythiol of high molecular weight; *Biochem. Pharmacol.*, 22:1179–88 (1973), both which are incorporated herein by reference. Alternatively, it is believed that the mercaptodextran can be made by polymerizing the dextran with a sulfur derivative such as mercaptosuccinic acid. In any event, it is not presently believed that the method of manufacturing is critical to the practice of the present invention. Thus, the mercaptodextran can be prepared by any suitable method.

It is believed that the dextran can have any molecular weight from about 500 to about 500,000 and therefore, the resulting mercaptodextran may also have any suitable molecular weight from about 500 to about 500,000 such that the mercaptodextran exhibits tyrosinase inhibition. In this regard, it is believed that the mercapotdextrans having a molecular weight less than about 100,000 may be more effective for skin whitening than those having a molecular weight greater than about 100,000. Consequently, it is preferred to use a mercaptodextran having a molecular weight between about 1000 and 100,000. In a preferred embodiment, a mercaptodextran from Pharmacia Biotech and having a molecular weight of about 10,000 is known to be effective.

When the mercaptodextran is mixed with bearberry extract and its reducing agent, as well as with other known whitening agents, the ratio of the mercaptodextran to the bearberry extract is from about 1:100 to about 100:1, preferably from about 1:50 to about 50:1, more preferably from about 1:10 to about 10:1. Most preferably, the ratio of mercaptodextran to the bearberry extract is from about 1:5 to about 5:1.

The compositions of the present invention may be prepared in various forms. For example, they may be in the form of a cosmetic preparation such as an emulsion, liniment or ointment lotions, creams, (both oil-in-water, water-in-oil, and multiple phase), solutions, suspensions (anhydrous and water based), anhydrous products (both oil and glycol based), gels, sticks, surfactant systems (cleansers, shampoos, facial washes, etc.), powders, masks, pack or powder, or the like.

The compositions of the present invention generally include bearberry extract, a reducing agent and a cosmetically acceptable or pharmaceutically acceptable carrier. The terms "pharmaceutically acceptable" and "cosmetically acceptable" means those drugs, medicaments, or inert ingredients which are suitable for use in contact with the tissues of humans and lower animals without undue toxicity, incompatibility, instability, irritation, and the like, commensurate with a reasonable benefit/risk ratio.

The cosmetically acceptable vehicle will usually form from about 1% to about 99.9%, preferably from about 50% to about 99% by weight of the composition, and can. in the absence of other cosmetic adjuncts, form the balance of the composition.

The compositions generally will contain various known conventional cosmetic ingredients. For example, cosmetic ingredients such as alcohols, fats and oils, surfactants, fatty acids, silicone oils, humectants, moisturizers, viscosity modifiers, emulsifiers, stabilizers, coloring agents, and perfumes may be included.

Emollients include stearyl alcohol, glyceryl monoricinoleate, glyceryl monostearate, mink oil, cetyl alcohol, isopropyl isostearate, fatty acids and esters, stearic acid, isobutyl palmitate, isocetyl stearate, oleyl alcohol, isopropyl laurate, hexyl laurate, decyl oleate, octadecan-2-ol, isocetyl alcohol, fatty alcohols such as eicosanyl alcohol, behenyl alcohol, cetyl palmitate, volatile or non-volatile silicone oils such as dimethylpolysiloxane, di-n-butyl sebacate, isopropyl myristate, isopropyl palmitate, isopropyl stearate, butyl stearate, polyethylene glycol, triethylene glycol, lanolin, lecithin, cocoa butter, corn oil, cotton seed oil, tallow, lard, olive oil, palm kernel oil, rapeseed oil, safflower seed oil, evening primrose oil, soybean oil, sunflower seed oil, passion flower oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate.

The composition according to the invention can optionally comprise one or more oils or other materials having the properties of an oil. Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Although the composition of the invention can be anhydrous, it can also comprise water, usually up to 98%, preferably from 5 to 80% by volume.

The composition of the invention can also optionally comprise a high molecular weight silicone surfactant, which can also act as an emulsifier, in place of or in addition to the optional emulsifier(s) already mentioned.

The silicone surfactant may be a high molecular weight polymer of dimethyl polysiloxane with polyoxyethylene and/or polyoxypropylene side chains having a molecular weight of from 10,000 to 50,000 and having the structure:

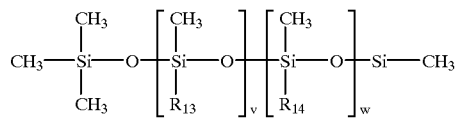

where the groups $R_{13}$ and $R_{14}$ are each chosen from —H, $C_{1-8}$ alkyl and

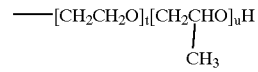

t has a value of from 9 to 115,
u has a value of from 0 to 50,
v has a value of from 133 to 673,
w has a value of from 25 to 0.25.

The dimethyl polysiloxane polymer may provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane. Examples of the volatile siloxanes, in which the polysiloxane polymer can be dispersed include polydimethyl siloxane (pentamer and/or hexamer). An example of a silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Examples of conventional adjuncts that can optionally be employed include humectants, such as glycerol, sorbitol, 2-pyrrolidone-5-carboxylate, dibutylphthalate, gelatin, polyethylene, glycol, preferably PEG 200–600; buffers, such as lactic acid together with a base such as triethanolamine or sodium hydroxide; surfactants, such as glycerol ethers; waxes, such as beeswax, paraffin wax, plant extracts, such as Aloe vera, cornflower, witch hazel, elderflower, thickeners such as xanthan gum, activity enhancers; colorants, perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane; and skin benefit agents, such as retinoic acid, retinol, retinol esters; anti-inflammatory agents, such as salicylic acid; and mixtures thereof.

Skin permeation ingredients such as α- and β-hydroxy acids may also be included. Mollifying agents such as lipids, ceramides, sphingosines, sphingolipids, pseudoceramides, phospholipids, and glycolipids may also be included. These mollifying agents may act to mollify the irritating effect of one or more substances in the formulations. In addition, they may aid in preserving and repairing the barrier function of the skin. The mollifying agents may be combined with sterols, such as cholesterol and cholesterol sulfate, and fatty acids, particularly those that may be found in the skin and hair such as the $C_{10}$–$C_{30}$ fatty acids.

In another aspect of the composition of the present invention, there is provided a bearberry-containing skin whitening composition, wherein the improvement comprises adding an effective amount of a reducing agent to increase the skin-whitening efficacy of the bearberry extract. The reducing agent includes the formaldehyde compounds described above.

In the whitening compositions and methods according to the present invention, the amounts of bearberry extract and its reducing agent cannot be absolutely specified because it varies according to the form of the preparation. However, bearberry is generally used in an amount from about 0.001% to about 99%, preferably from about 0.01% to about 50%, desirably from about 0.1% to about 25%, more preferably from about 0.2% to about 10%, most preferably from about 1% to about 5% based on the whole weight of the whitening composition.

The reducing agent is generally used in an amount from about 0.001% to about 99%, preferably from about 0.01% to about 50%, desirably from about 0.1% to about 25%, more preferably from about 0.01% to about 1.00%, and most preferably from about 0.10% to about 0.50% based on the whole weight of the whitening composition.

Within these ranges, the ratio of bearberry extract to reducing agent is from about 1:1000 to about 1000:1, preferably from about 1:100 to about 100:1, more preferably from about 1:10 to 10:1.

In another aspect of the composition of the present invention, the composition comprises bearberry extract and a reducing agent, wherein the reducing agent is present in an amount effective to increase the skin-whitening efficacy of the bearberry extract. Again, the reducing agent includes the formaldehyde compounds described above.

The present invention also contemplates a method of visibly whitening human skin comprising applying to the skin a composition containing bearberry extract and an effective amount of a reducing agent wherein the composition is applied in an amount and for a period of time sufficient to visibly whiten the skin. Preferably, the method comprises topically applying to the skin a composition comprising bearberry extract, a reducing agent, and a pharmaceutically acceptable carrier or a cosmetically acceptable carrier.

The present invention also contemplates a method of increasing the skin-whitening efficacy of a skin-whitening composition containing bearberry extract, the method comprising adding an effective amount of a reducing agent. The composition is applied in an amount and for a period of time sufficient to visibly whiten the skin.

To demonstrate the effectiveness of a skin whitening composition containing bearberry extract and a reducing agent according to the present invention, the following test was conducted.

EXAMPLE 1

Two skin whiteners that contained 2.00% of bearberry extract were applied to a petri dish containing cultured melanocytes for 48 h. One skin whitener contained the 0.30% of the reducing agent diazolidinyl urea, and the other did not. When viewed with the eye, the sample to which skin whitener that contained the reducing agent was applied surprisingly appeared whiter as compared to the sample to which skin whitener that did not contain the reducing agent.

EXAMPLE 2

The following is an example of an oil-in-water emulsion composition according the present invention.

| RAW MATERIAL | % |
|---|---|
| WATER, PURIFIED | 85.2 |
| XANTHAN GUM | 0.5 |
| GLYCERIN | 4.8 |
| TITANIUM DIOXIDE | 0.2 |
| SQUALANE | 3.0 |
| SOYBEAN OIL | 1.0 |
| STEARIC ACID AND BEHENYL ALCOHOL AND GLYCERYL STEARATE AND MALEATED SOYBEAN OIL AND LECITHIN AND $C_{12-16}$ ALCOHOLS AND PALMITIC ACID | 0.5 |
| ACEROLA CHERRY FERMENTATE | 0.3 |
| ORANGE EXTRACT | 1.0 |
| LEMON EXTRACT & CUCUMBER EXTRACT & SODIUM CITRATE | 0.5 |
| BEARBERRY EXTRACT | 2.0 |
| REDUCING AGENT (PROPYLENE GLYCOL AND DIAZOLIDINYL UREA AND METHYLPARABEN AND PROPYLPARABEN | 1.0 |
| TOTAL | 100.0 |

It should be understood that a wide range of changes and modifications could be made to the embodiments described above. It is therefore intended that the foregoing description illustrates rather than limits this invention, and that it is the following claims, including all equivalents, which define this invention.

What is claimed:

1. A composition for topical use that has a melanin synthesis-inhibiting activity, the composition comprising bearberry extract and a reducing agent, wherein the reducing agent is present in an amount effective to increase the skin-whitening efficacy of the bearberry extract and the bearberry extract is from *Arctostaphylos uva-ursi* and is a glycolic extract standardized to >50 tyrosinase inhibition units per milliliter.

2. The composition of claim 1 wherein the reducing agent is a formaldehyde donating compound.

3. The composition of claim 2 wherein the formaldehyde donating compound is selected from the group consisting of formaldehyde, 2-bromo-2-nitropropane-1,3-diol, glutaraldehyde, quaternium-15, polymethoxybicylic oxazolidine, DM hydantoin, MDM hydantoin, DMDM hydantoin, allantoin-formaldehyde condensation products and mixtures thereof.

4. The composition of claim 1 wherein the composition comprises from about 0.001% to about 99% by weight of bearberry extract.

5. The composition of claim 1 wherein the composition comprises from about 0.001% to about 99% by weight of the reducing agent.

6. The composition of claim 1 wherein the composition is in the form of a preparation selected from the group consisting of cream, ointment, foam, lotion, plaster, tablets, granules, and emulsion.

7. The composition of claim 1 further comprising a skin-whitening agent selected from the group of tyrosinase inhibitors, free radical scavengers, chelating agents and mixtures thereof.

8. The composition of claim 7 wherein the tyrosinase inhibitors are selected from the group consisting of arbutin, lemon extract, cucumber extract, mercaptosuccinic acid, mercaptodextran, kojic acid, derivatives of kojic acid, vitamin C, derivatives of vitamin C, hydroquinone, glutathione, cysteine, mulberry extract, licorice extract and its derivatives, and mixtures thereof.

9. In a skin-whitening composition containing bearberry extract from *Arctostaphylos uva-ursi* and is a glycolic extract standardized to >50 tyrosinase inhibition units per milliliter, the improvement comprising an amount of a reducing agent effective to increase the skin-whitening efficacy of the bearberry extract.

10. A method of visibly whitening human skin comprising applying on the skin a composition containing bearberry extract from *Arctostaphylos uva-ursi* and is a glycolic extract standardized to >50 tyrosinase inhibition units per milliliter and an effective amount of a reducing agent, whereby the composition is applied in an amount and for a period of time sufficient to visibly whiten the skin.

11. The method of claim 10 wherein the reducing agent is a formaldehyde donating compound.

12. The method of claim 11 wherein the formaldehyde donating compound is selected from the group consisting of formaldehyde, 2-bromo-2-nitopropane-1,3-diol, glutaraldehyde, quaternium-15, polymethoxybicylic oxazolidine, DM hydantoin, MDM hydantoin, DMDM hydantoin, and allantoin-formaldehyde condensation products and mixtures thereof.

13. The method of claim 10 wherein the composition comprises from about 0.001% to about 99% by weight of bearberry extract.

14. The method of claim 10 wherein the composition comprises from about 0.001% to about 99% by weight of the reducing agent.

15. A method of increasing the skin-whitening efficacy of a skin-whitening composition containing bearberry extract from *Arctostaphylos uva-ursi* and is a glycolic extract standardized to >50 tysoniase inhibition units per milliliter, the method comprising adding an effective amount of a reducing agent.

16. The method of claim 15 wherein the reducing agent is a formaldehyde donating compound.

17. The method of claim 16 wherein the formaldehyde donating compound is selected from the group consisting of formaldehyde, 2-bromo-2-nitopropane-1,3-diol, glutaraldehyde, quaternium-15, polymethoxybicylic oxazolidine, DM hydantoin, MDM hydantoin, DMDM hydantoin, and allantoin-formaldehyde condensation products and mixtures thereof.

18. The method of claim 15 wherein the composition comprises from about 0.001% to about 99% by weight of bearberry extract.

19. The method of claim 15 wherein the composition comprises from about 0.001% to about 99% by weight of the reducing agent.

* * * * *

UNITED STATES PATENT AND TRADEMARK OFFICE
CERTIFICATE OF CORRECTION

PATENT NO. : 5,980,904
DATED : November 9, 1999
INVENTOR(S) : Jessie C. Leverett and Jeffrey M. Dornoff It is certified that error appears in the above-identified patent and that said Letters Patent is hereby corrected as shown below:

Title page, item [56],
Under Foreign Patent Documents, Change "50288 7/1981 Hungary" to -- 50288 1/1990 Hungary --

Column 1,
Line 58, Change "nitopropane" to -- nitropropane --

Column 2,
Line 44, "nitopropane" to -- nitropropane --

Claim 3, column 8,
Line 40, Change "nitopropane" to -- nitropropane --

Claim 12, column 9,
Line 16, Change "nitopropane" to -- nitropropane --

Claim 15, column 10,
Line 4, Change "tysoniase" to -- tyrosinase --

Claim 17, column 10,
Line 12, Change "nitropropane" to -- nitropropane --

Signed and Sealed this

Eighteenth Day of September, 2001

Attest:

NICHOLAS P. GODICI
Attesting Officer    Acting Director of the United States Patent and Trademark Office